United States Patent
Stauss et al.

(10) Patent No.: US 8,722,048 B2
(45) Date of Patent: May 13, 2014

(54) T-CELL RECEPTOR CAPABLE OF RECOGNISING AN ANTIGEN FROM CYTOMEGALOVIRUS

(75) Inventors: Hans Stauss, London (GB); Shao-An Xue, London (GB)

(73) Assignee: UCL Business PLC, London (GB)

( * ) Notice: Subject to any disclaimer, the term of this patent is extended or adjusted under 35 U.S.C. 154(b) by 0 days.

(21) Appl. No.: 13/498,564

(22) PCT Filed: Sep. 29, 2010

(86) PCT No.: PCT/GB2010/001820
§ 371 (c)(1), (2), (4) Date: May 16, 2012

(87) PCT Pub. No.: WO2011/039507
PCT Pub. Date: Apr. 7, 2011

(65) Prior Publication Data
US 2013/0045221 A1    Feb. 21, 2013

(30) Foreign Application Priority Data
Sep. 29, 2009 (GB) .................................. 0917094.5

(51) Int. Cl.
A61K 39/42 (2006.01)
C07K 14/725 (2006.01)
C07K 14/045 (2006.01)

(52) U.S. Cl.
CPC ........... *C07K 14/7051* (2013.01); *C07K 14/045* (2013.01); *C12N 2799/027* (2013.01)
USPC ..................................................... 424/147.1

(58) Field of Classification Search
None
See application file for complete search history.

(56) References Cited

U.S. PATENT DOCUMENTS 5,830,755 A    11/1998    Nishimura et al.

FOREIGN PATENT DOCUMENTS

| EP | 0879282 B1 | 7/2003 |
| EP | 1127068 B1 | 1/2006 |
| EP | 1619202 A2 | 1/2006 |
| EP | 1339745 B1 | 1/2007 |
| EP | 1619202 B1 | 8/2008 |
| WO | WO-97/26328 A1 | 7/1997 |
| WO | WO-00/26249 A1 | 5/2000 |
| WO | WO-02/44207 A1 | 6/2002 |
| WO | WO-2005/056595 A2 | 10/2005 |
| WO | WO 2007131092 A2 * | 11/2007 |

OTHER PUBLICATIONS

Carlsson et al. British Journal of Haematology, 2003, 121, 428-438.*
Janeway et al., Immunobiology, 5th Ed., Garland Science, pp. 106-108, 117-118 and 260-263, (2001)).*
Manning et al., Immunity, vol. 8, 413-425, Apr. 1998.*
Garcia et al., Cell, vol. 122, 333-336, Aug. 12, 2005.*
Goyarts et al. (Mol Immunol. Jul. 1998;35(10):593-607).*
Trautmann et al. (The Journal of Immunology, 2005, 175: 6123-6132).*
Arden et al. (Immunogenetics (1995) 42:455-500).*
Genbank locus S03494, clone HBP34, Jul. 23, 1999, pp. 1-2.*
Genbank locus AAA60669, Jan. 13, 1995, T-cell receptor beta-chain J1.2, p. 1.*
Genbank locus HUMTCRADCV, Oct. 25, 2001, TCR receptor alpha chain, J49 segment, pp. 1-33.*
Genbank locus AAB69034, Mar. 9, 2009, TCRAV17S1, pp. 1-2.*
Szymczak et al. (Nature Biotechnology vol. 22 Number May 5, 2004, pp. 589-594).*
Altschul et al., Basic local alignment search tool. *J. Mol. Biol.*, 215(3):403-10 (1990).
Ausubel (Ed) et al., Short Protocols in Molecular Biology, 4th Edition, Chapter 18—Unit 18.1, pp. 18.1-18.23 (1999).
Ausubel (Ed) et al., Short Protocols in Molecular Biology, 4th Edition, Chapter 7—Unit 7.7, pp. 7.58-7.60 (1999).
Celis et al., Identification of potential CTL epitopes of tumor-associated antigen MAGE-1 for five common HLA-A alleles. *Mol. Immunol.*, 31(18):1423-30 (1994).
Coffin (Ed.) et al., Retroviruses, pp. 758-763 (1997).
Devereux et al., A comprehensive set of sequence analysis programs for the VAX. *Nucleic Acids Res.*, 12(1 Pt 1):387-95 (1984).
Gakamsky et al., Kinetic evidence for a ligand-binding-induced conformational transition in the T cell receptor. *Proc. Natl. Acad. Sci. U.S.A.*, 104(42):16639-44 (2007).
Gras et al., Structural bases for the affinity-driven selection of a public TCR against a dominant human cytomegalovirus epitope. *J. Immunol.*, 183(1):430-7 (2009).
He et al., High frequencies cytomegalovirus pp65(495-503)-specific CD8+ T cells in healthy young and elderly Chinese donors: characterization of their phenotypes and TCR Vbeta usage. *J. Clin. Immunol.*, 26(5):417-29 (2006).
Hildinger et al., Design of 5' untranslated sequences in retroviral vectors developed for medical use. *J. Virol.*, 73(5):4083-9 (1999).
Lewis et al., Human immunodeficiency virus infection of cells arrested in the cell cycle. *EMBO J.*, 11(8):3053-8 (1992).
Luo et al., Analysis of the conservation of T cell receptor alpha and beta chain variable regions gene in pp65 peptide-specific HLA-A 0201-restricted CD8+ T cells. *Cell Mol. Immunol.*, 6(2):105-10 (2009).

(Continued)

*Primary Examiner* — Zachary Skelding
(74) *Attorney, Agent, or Firm* — Marshall, Gerstein & Borun LLP

(57) ABSTRACT

The present invention provides a T-cell receptor (TCR) which binds to a peptide from the cytomegalovirus (CMV) phosphoprotein pp65 having the amino acid sequence NLVPMVATV (SEQ ID No. 1) when presented by a major histocompatability complex (MHC) molecule. The present invention also provides a nucleotide sequence encoding such a TCR, a vector comprising such a nucleotide sequence and its use to produce a CMV-specific T-cell. The present invention also provides the use of CMV-specific T-cell for cellular immunotherapy.

4 Claims, 5 Drawing Sheets

(56) References Cited

OTHER PUBLICATIONS

McLaughlin-Taylor et al., Identification of the major late human cytomegalovirus matrix protein pp65 as a target antigen for CD8+ virus-specific cytotoxic T lymphocytes. *J. Med. Virol.*, 43(1):103-10 (1994).

Schub et al., CMV-specific TCR-transgenic T cells for immunotherapy. *J. Immunol.*, 183(10):6819-30 (2009).

Stauss et al., Monoclonal T-cell receptors: New reagents for cancer therapy, *Molec. Ther.*, pp. 1-7, advanced only publication Jul. 17, 2007.

Tatusova et al., BLAST 2 Sequences, a new tool for comparing protein and nucleotide sequences. *FEMS Microbiol. Lett.*, 174(2):247-50 (1999).

Tatusova et al., Erratum to "BLAST 2 sequences, a new tool for comparing protein and nucleotide sequences". *FEMS Microbiol. Lett.*, 177: 187-8 (1999).

International Search Report and Written Opinion of the International Searching Authority issued in connection with International Application No. PCT/GB2010/001820, dated Feb. 9, 2011.

International Preliminary Report on Patentability issued in connection with International Application No. PCT/GB2010/001820, completed Apr. 3, 2012.

\* cited by examiner

T-CELL RECEPTOR CAPABLE OF RECOGNISING AN ANTIGEN FROM CYTOMEGALOVIRUS

This application is the U.S. National Stage of International Application No. PCT/GB2010/001820, incorporated by reference, filed Sept. 29, 2010, which claims the priority benefit of Great Britain Application No. 0917094.5, filed Sept. 29, 2009.

FIELD OF THE INVENTION

The present invention relates to a T-cell receptor (TCR) capable of recognising an antigen from Cytomegalovirus (CMV). The present invention also relates to the use of TCR gene transfer to produce CMV-specific T cells and their use to treat and/or prevent CMV disease.

BACKGROUND TO THE INVENTION

Cytomegalovirus is a frequent pathogen in humans and is usually associated with asymptomatic primary infection, followed by a state of viral persistence or latency. In patients with congenital or acquired immune deficiencies and those undergoing solid organ or bone marrow transplantation, primary CMV infection and reactivation of persistent CMV have frequently been associated with life-threatening invasive visceral disease.

Reactivation of the latent human herpes virus, Cytomegalovirus (CMV) post allogeneic haematopoietic stem cell transplantation (Allo-HSCT) can result in significant morbidity and mortality unless treated promptly. Anti-viral therapy is usually effective, but has serious side effects, such as myelosuppression (Ganciclovir™) or nephrotoxicity (Foscarnet™).

Cellular immunotherapy for CMV has been tested in Phase I/II trials in the UK and Europe. In these trials CMV-specific T cells were isolated from the peripheral blood of CMV seropositive donors and re-infused into recipients following CMV reactivation resulting in sustained anti-viral responses. Post-transplant recovery of CD8$^+$ CMV-specific cytotoxic T-cells (CTL) abrogates the development of CMV-related disease. An advantage of cellular therapy for CMV reactivation is the transfer of immunological memory, which can reduce the number of subsequent reactivations.

Increasing numbers of highly immunosuppressive (or T cell depleted) reduced intensity conditioning Allo-HSCTs are being performed in the UK. Such approaches reduce the toxicity of transplantation in older patients with more co-morbidities. There are therefore more patients at risk of CMV reactivation post Allo-HSCT. Further, as these patients are older and have additional co-morbidities, making them less tolerant of currently available anti-viral drug therapy.

As approximately 50% of adult individuals have been previously infected with CMV, there are significant numbers of CMV 'mismatched' Allo-HSCT performed, where the donor is CMV seronegative and the recipient CMV seropositive. Transplant recipients with CMV seronegative donors do not benefit from cellular immunotherapy due to the lack of CMV-specific memory T cells. Such patients are therefore seriously at risk from complications arising from reactivation of latent CMV. At present, there is no reliable strategy to isolate virus specific T cells from uninfected naïve individuals, as the precursor frequency is low or absent and the in vitro priming of T-cell responses is inefficient.

There is thus a need for alternative methods to treat or prevent CMV disease, in particular reactivation of latent CMV post Allo-HSCT. There is also a need for an alternative source of CMV-specific T cells for cellular immunotherapy.

SUMMARY OF ASPECTS OF THE INVENTION

Figure 1:
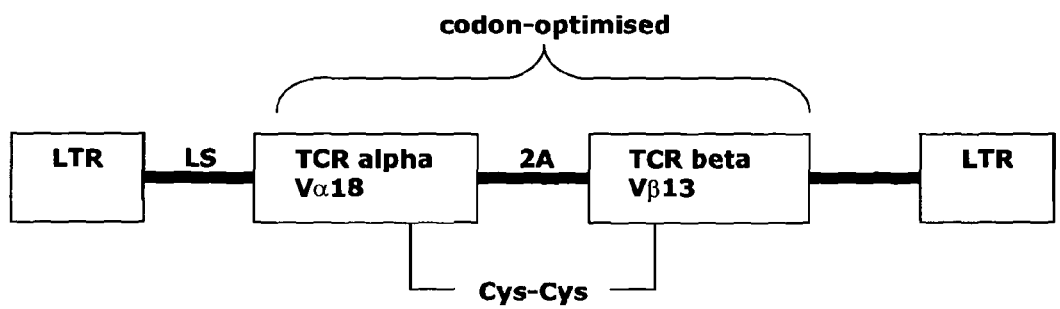
FIG. 1—Schematic of retroviral vector construct pMP71-pp65(alpha-2A-beta)-Cys1.

The present inventors have assembled a T-cell receptor that is specific for the major CMV matrix phosphoprotein pp65. They have also constructed a retroviral vector comprising the TCR α and β genes and used this to transduce human T cells. The cells were shown to express CMV pp65-specific TCR and show functional antigen specific activity.

The use of cellular therapy or TCR gene therapy offers several advantages over conventional antiviral therapies for the treatment of CMV disease.

The administration of anti-viral drug therapies in routine use require the patient to be an in-patient (Foscarnet™) or to attend day-care twice daily (Ganciclovir™). Ganciclovir can be administered via a CADD pump if available. There are NHS cost, health, social and psychological implications to this, particularly as duration of therapy is typically in excess of 2 weeks. In comparison, the use of cellular therapy requires a single infusion of T cells.

There is also the advantage that cellular therapy transfers immunological memory which, for example, reduces the number of subsequent CMV reactivations following allo-HSCT.

Thus, in a first aspect, the present invention provides a T-cell receptor (TCR) specific for the cytomegalovirus (CMV) phosphoprotein pp65.

The TCR may recognise the epitope NLVPMVATV (SEQ ID No. 1) from pp65.

The TCR may be capable of binding to a peptide having the amino acid sequence NLVPMVATV (SEQ ID No. 1) when presented by a major histocampatability complex (MHC) molecule.

The α chain and the β chain of the TCR each have three complementarity determining regions (CDRs). The α chain and the β chain of the TCR may have the following CDR3 sequences:

```
                                    (SEQ ID No. 2)
CDR3α - ARNTGNQFYFGTGTSLTVIPN (SEQ ID No. 3)
CDR3β - ASSFQTGASYGYTFGSGTRLTVL
``` or a variant of those sequences having up to three amino acid changes.

The CDRs of the α chain may having the following amino acid sequences:

CDR1α - SSNFYA (SEQ ID No. 4)

CDR2α - MTLNGD (SEQ ID No. 5)

CDR3α - ARNTGNQFYFGTGTSLTVIPN (SEQ ID No. 2)

or variants of those sequences having up to three amino acid changes.

The CDRs of the β chain may having the following amino acid sequences:

CDR1β - MNHEY (SEQ ID No. 6)

CDR2β - SVGAGI (SEQ ID No. 7)

CDR3β - ASSFQTGASYGYTFGSGTRLTVL. (SEQ ID No. 3)

or variants of those sequences having up to three amino acid changes.

The TCR of the first aspect of the invention may comprise the amino acid sequence shown as SEQ ID No. 8 or a variant thereof having at least 80% amino acid sequence identity.

The TCR of the first aspect of the invention may comprise one or more mutations at the TCR α chain/β chain interface, such that when the TCR α chain and β chain as defined in any preceding claim are expressed in a T-cell, the frequency of mis-pairing between these chains and the endogenous TCR α chain and β chain is reduced.

For example, in the TCR of the first aspect of the invention, the constant region domains of the α chain and β chain may each comprise an additional cysteine residue, enabling the formation of an extra disulphide bond between the α chain and the β chain.

The second aspect provides nucleotide sequences encoding all or a part of the TCR according to the first aspect of the invention.

A first embodiment of the second aspect of the invention relates to a nucleotide sequence encoding the α chain of a TCR according to the first aspect of the invention.

The nucleotide sequence of this first embodiment may comprise bases 1-780 of the nucleotide sequence shown as SEQ ID No. 9 or a variant thereof having at least 80% sequence identity.

A second embodiment of the second aspect of the invention relates to a nucleotide sequence encoding the β chain of a TCR according to the first aspect of the invention.

The nucleotide sequence of this second embodiment may comprise bases 870-1791 of SEQ ID No. 9 or a variant thereof having at least 80% sequence identity.

A third embodiment of the second aspect of the invention relates to a nucleotide sequence encoding a TCR α chain linked to a TCR β chain.

The nucleotide sequence may comprise the TCR α and β genes linked by an internal self-cleaving sequence.

The nucleotide sequence of this third embodiment may comprise the sequence shown as SEQ ID No. 9 or a variant thereof having at least 80% sequence identity.

In a third aspect, the present invention provides a vector comprising a nucleotide sequence according to the second aspect of the invention. The vector may, for example, be a retroviral vector.

In a fourth aspect, the invention provides a cell which comprises a nucleotide sequence according to the second aspect of the invention. The cell may, for example be a T-cell or a stem cell. The cell may be derived from a T-cell isolated from a subject.

In a fifth aspect the present invention provides a method for producing a cell according to the fourth aspect of the invention which comprises the step of transducing or transfecting a cell in vitro or ex vivo with a vector according to the third aspect of the invention.

The cell for transduction/transfection may be a T-cell from a CMV seronegative donor.

In a sixth aspect, the present invention provides a method for treating and/or preventing a disease associated with CMV in a subject which comprises the step of adoptive transfer of a CMV-specific T-cell to the subject, wherein the CMV-specific T-cell is made by TCR gene transfer.

The T-cell comprises one or more heterologous nucleotide sequence(s) capable of encoding a CMV-specific TCR.

The TCR may be in accordance with the first aspect of the invention.

The method may be used to treat or prevent reactivation of CMV post allogeneic haematopoietic stem cell transplantation (Allo-HSCT).

The method may be used to treat or prevent reactivation of CMV post solid organ transplantation (e.g. kidney, liver, pancreas, bowl, cornea) or cell transplantation (islet cell, limbal stem cells, stem cell therapy).

The CMV-specific T cell may be derived from the subject or from a donor subject.

In the method of the sixth aspect of the invention, viral load may be monitored (i) before treatment, to determine the appropriate time for treatment; and/or (ii) after treatment, to analyse the effect of the treatment.

Viral load may be monitored, for example, using a PCR-based assay.

The present invention also provides a vector according to the third aspect of the invention or a cell according to the fourth aspect of the invention for use in treating and/or preventing a disease associated with CMV in a subject.

The present invention also provides a pharmaceutical composition comprising a vector according to the third aspect of the invention or a cell according to the fourth aspect of the invention.

The present invention also provides the use of a TCR according to the first aspect of the invention, a nucleotide sequence according to the second aspect of the invention, a vector according to the third aspect of the invention, or a cell according to the fourth aspect of the invention in the manufacture of a medicament for use in treating and/or preventing a disease associated with CMV in a subject.

DETAILED DESCRIPTION

T-Cell Receptor

During antigen processing, antigens are degraded inside cells and then carried to the cell surface by major histocompatability complex (MHC) molecules. T cells are able to recognise this peptide: complex at the surface of the antigen presenting cell. There are two different classes of MHC molecules: MHC I and MHC II, that deliver peptides from different cellular compartments to the cell surface.

The T cell receptor or TCR is the molecule found on the surface of T cells that is responsible for recognizing antigens bound to MHC molecules. The TCR heterodimer consists of an alpha and beta chain in 95% of T cells, whereas 5% of T cells have TCRs consisting of gamma and delta chains.

Engagement of the TCR with antigen and MHC results in activation of its T lymphocyte through a series of biochemical events mediated by associated enzymes, co-receptors, and specialized accessory molecules.

Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end.

The variable domain of both the TCR α-chain and β-chain have three hypervariable or complementarity determining regions (CDRs). CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule.

The constant domain of the TCR domain consists of short connecting sequences in which a cysteine residue forms a disulfide bond, making a link between the two chains. The TCR of the present invention may have an additional cysteine residue in each of the α and β chains such that the TCR comprises two disulphide bonds in the constant domains (see below).

The structure allows the TCR to associate with other molecules like CD3 which possess three distinct chains (γ, δ, and ε) in mammals and the ζ-chain. These accessory molecules have negatively charged transmembrane regions and are vital to propagating the signal from the TCR into the cell. The CD3- and ζ-chains, together with the TCR, form what is known as the T cell receptor complex.

The signal from the T cell complex is enhanced by simultaneous binding of the MHC molecules by a specific co-receptor. On helper T cells, this co-receptor is CD4 (specific for class II MHC); whereas on cytotoxic T cells, this co-receptor is CD8 (specific for class I MHC). The co-receptor not only ensures the specificity of the TCR for an antigen, but also allows prolonged engagement between the antigen presenting cell and the T cell and recruits essential molecules (e.g., LCK) inside the cell involved in the signaling of the activated T lymphocyte.

The term "T-cell receptor" is thus used in the conventional sense to mean a molecule capable of recognising a peptide when presented by an MHC molecule. The molecule may be a heterodimer of two chains α and β (or optionally γ and δ) or it may be a single chain TCR constuct.

The present invention also provides the α chain or β chain from such a T cell receptor.

The TCR of the present invention may be a hybrid TCR comprising suences derived from more than one species. For example, it has surprisingly been found that murine TCRs have been found to be more efficiently expressed in human T cells than human TCRs. The TCR may therefore comprise human variable regions and murine constant regions. A disadvantage of this approach is that the murine constant sequences may trigger an immune response, leading to rejection of the transferred T cells. However, the conditioning regimens used to prepare patients for adoptive T-cell therapy may result in sufficient immunosuppression to allow the engraftment of T cells expressing murine sequences.

CDR Sequences

The TCR of the first aspect of the invention comprises two chains (α and β) each of which comprise three complementarity determining regions.

T-cell receptor diversity is focused on CDR3 and this region is primarily responsible for antigen recognition. The sequences of the CDR3 regions from the TCR of the present invention may be:

```
                                             (SEQ ID No. 2)
        CDR3α - ARNTGNQFYFGTGTSLTVIPN (SEQ ID No. 3)
        CDR3β - ASSFQTGASYGYTFGSGTRLTVL
``` or as variant of those sequences having up to three amino acid changes.

The α chain may comprise CDRs having the following amino acid sequences:

```
                                             (SEQ ID No. 4)
        CDR1α - SSNFYA (SEQ ID No. 5)
        CDR2α - MTLNGD (SEQ ID No. 2)
        CDR3α - ARNTGNQFYFGTGTSLTVIPN.
```

The β chain may comprise CDRs having the following amino acid sequences:

```
                                             (SEQ ID No. 6)
        CDR1β - MNHEY (SEQ ID No. 7)
        CDR2β - SVGAGI (SEQ ID No. 3)
        CDR3β - ASSFQTGASYGYTFGSGTRLTVL.
```

The CDRs may comprise one or more "changes", such as substitutions, additions or deletions from the given sequence, provided that the TCR retains the capacity to bind the pp65 epitope:MHC complex. The change may involve substitution of an amino acid for a similar amino acid (a conservative substitution). A similar amino acid is one which has a side chain moiety with related properties as grouped together, for example as shown below:

(i) basic side chains: lysine, arginine, histidine
(ii) acidic side chains: aspartic acid and glutamic acid
(iii) uncharged polar side chains: aspargine, glutamine, serine, threonine and tyrosine
(iv) non-polar side chains: glycine, alanine, valine, leucine, isoleucine, proline, phenylalanine, methionine, tryptophan and cysteine.

Any amino acid changes should maintain or improve the capacity to bind MHC molecules. For example, if the peptide is capable of binding MHC molecules of the HLA-A*0201 allele then it is preferred that the amino acids at position 2 of the peptide (i.e. the second amino acid from the N-terminus) are leucine or methionine, although isoleucine, valine, alanine and threonine are also tolerated. It is also preferred that the amino acid at position 9 or 10 is valine, leucine or isoleucine, although alanine, methionine and threonine are also tolerated. The preferred MHC binding motifs or other HLA alleles are disclosed in Celis et al, Molecular Immunology, Vol. 31, 8, Dec. 1994, pages 1423 to 1430.

The TCR of the first aspect of the invention may comprise the following amino acid sequence (SEQ ID No. 8) or a variant thereof having at least 70%, 80%, 90%, or 95% amino acid sequence identity:

CMVa18-p2A-Vb13-aa:

```
MEKNPLAAPL LILWFHLDCV SILNVEQSPQ SLHVQEGDST

NFTCSFPSSN FYALHWYRWE TAKSPEALFV MTLNGDEKKK
GRISATLNTK EGYSYLYIKG SQPEDSATYL CARNTGNQFY
FGTGTSLTVI PNIQNPDPAV YQLKDPRSQD STLCLFTDFD
SQINVPKTME SGTFITDKCV LDMKAMDSKS NGAIAWSNQT
SFTCQDIFKE TNATYPSSDV PCDATLTEKS FETDMNLNFQ
NLSVMGLRIL LLKVAGFNLL MTLRLWSSGS GATNFSLLKQ
AGDVEENPGP MVIGLLCCAA LSLLWAGPVN AGVTQTPKFQ
VLKTGQSMTL QCAQDMNHEY MSWYRQDPGM GLRLIHYSVG
AGITDQGEVP NGYNVSRSTT EDFPLRLLSA APSQTSVYFC
ASSFQTGASY GYTFGSGTRL TVLEDLRNVT PPKVSLFEPS
KAEIANKQKA TLVCLARGFF PDHVELSWWV NGKEVHSGVC
TDPQAYKESN YSYCLSSRLR VSATFWHNPR NHFRCQVQFH
GLSEEDKWPE GSPKPVTQNI SAEAWGRADC GITSASYHQG
VLSATILYEI LLGKATLYAV LVSGLVLMAM VKKKNS*
```

Blue: Constant sequences.

Red: cysteine molecules for the interchain disulphide bound.

Pink: 2A sequences.

Black: Variable sequences & CDR1,2,3 regions.

Variant sequences may comprise amino acid additions, deletions and/or insertions. The variation may be concentrated in one or more regions, such as the constant regions, the linker, or the framework regions of the α or β clains, or they may be spread throughout the molecule.

Identity comparisons can be conducted by eye, or more usually, with the aid of readily available sequence comparison programs. These commercially available computer programs can calculate % identity between two or more sequences.

% identity may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % identity therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, for some applications, it is preferred to use the GCG Bestfit program. BLAST 2 Sequences is also available for comparing protein and nucleotide sequences (see FEMS Microbiol Lett 1999 174(2): 247-50; FEMS Microbiol Lett 1999 177(1): 187-8 and tatiana@ncbi.nlm.nih.gov).

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

CMV Phosphoprotein PP65

The first aspect of the invention relates to a TCR which binds specifically to peptide derivable from the major CMV matrix phosphoprotein pp65.

Matrix protein pp65 has been identified as a target antigen for CD8+ virus-specific cytotoxic T lymphocytes (McLaughlin-Taylor et al (1994) J. Med. Virol. 43:103-110). It has the sequence given below:

```
  1 masvlgpisg hvlkavfsrg dtpvlphetr llqtgihvrv sqpslilvsq ytpdstpchr 61 gdnqlqvqht yftgsevenv svnvhnptgr sicpsqepms iyvyalplkm lnipsinvhh 121 ypsaaerkhr hlpvadavih asgkqmwqar ltvsglawtr qqnqwkepdv yytsafvfpt 181 kdvalrhvvc ahelvcsmen tratkmqvig dqyvkvyles fcedvpsgkl fmhvtlgsdv 241 eedltmtrnp qpfmrphern gftvlcpknm iikpgkishi mldvaftshe hfgllcpksi 301 pglsisgnll mngqqiflev qairetvelr qydpvaalff fdidlllqrg pqysehptft 361 sqyriqgkle yrhtwdrhde gaaqgdddvw tsgsdsdeel vtterktprv tgggamagas 421 tsagrkrksa ssatactagv mtrgrlkaes tvapeedtde dsdneihnpa vftwppwqag 481 ilarnlvpmv atvqgqnlky qeffwdandi yrifaelegv wqpaaqpkrr rhrqdalpgp 541 ciastpkkhr g
```

The peptide NLVPMVATV recognised by the T-cell receptor of the first aspect of the invention is shown in red.

The TCR may recognise all or part of this sequence. The TCR may recognise a part of this sequence together with one or more (for example up to 5) upstream or downstream amino acids. The TCR may recognise all or part of the following sequence GILARNLVATVQGQNL.

Major Histocompatability Complex (MHC) Molecules

The TCR binds to the peptide as a peptide:MHC complex.

The MHC molecule may be an MHC class I or II molecule. The complex may be on the surface of an antien presenting cell, such as a dendritic cell or a B cell, or it may be immobilised by, for example, coating on to a bead or plate.

The human leukocyte antigen system (HLA) is the name of the major histocompatibility complex (MHC) in humans and includes that HLA class I antigens (A, B & C) and HLA class II antigens (DP, DQ, & DR).

The TCR of the present invention may, for example be HLA-A*0201-restricted.

Reducing Mispairing

The TCR of the first aspect of the invention may be expressed in a T cell to alter its antigen specificity. TCR-transduced T cells express at least two TCR alpha and two TCR beta chains. While the endogenous TCR alpha/beta chains form a receptor that is self-tolerant, the introduced TCR alpha/beta chains form a receptor with defined specificity for the given target antigen.

However, mis-pairing between endogenous and introduced chains may occur to form novel receptors, which might display unexpected specificities for self-antigens and cause autoimmune damage when transferred into patients.

Hence, several strategies have been explored to reduce the risk of mis-pairing between endogenous and introduced TCR chains. Mutations of the TCR alpha/beta interface is one strategy currently employed to reduce unwanted mis-pairing.

For example, the introduction of an additional cysteine in the constant domains of the alpha and beta chain allows the formation of an additional disulfide bond and enhances the pairing of the introduced chains while reducing mis-pairing with wild type chains.

The TCR of the present invention may therefore comprise an additional cysteine in the α chain and the β chain, which form an additional disulphide bond between the two chains, making two disulphide bonds in total.

The additional cysteines are shown in red in the amino acid sequence shown above in the Section "CDR sequences"

Nucleotide Sequence

The second aspect of the invention relates to a nucleotide sequence encoding a TCR receptor of the first aspect of the invention or a part thereof, such as one or more CDR; the variable sequence of the α chain or the β chain; the α chain and/or the β chain.

The nucleotide sequence may be double or single stranded, and may be RNA or DNA.

The nucleotide sequence may be codon optimised. Different cells differ in their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation may also involve the removal of mRNA instability motifs and cryptic splice sites.

The nucleotide sequence of the second aspect of the invention may comprise all or part of the following sequence (SEQ ID No. 9) or a variant thereof having at least 70%, 80%, 90%, or 95% amino acid sequence identity:

```
CMVa18-p2A-Vb13-coding seq:
ATGGAAAAGA ACCCCCTGGC TGCACCCCTG CTGATCCTGT

GGTTCCACCT GGACTGCGTG AGCATCCTGA ACGTGGAGCA

GAGCCCCCAG TCTCTGCATG TGCAGGAAGG CGACAGCACC

AACTTCACCT GCAGCTTCCC CAGCAGCAAC TTCTACGCCC

TGCACTGGTA CAGATGGGAG ACCGCCAAGA GCCCCGAGGC

CCTGTTCGTG ATGACCCTGA ACGGCGACGA GAAGAAGAAG
```

-continued
```
GGCCGGATCA GCGCCACCCT GAACACCAAA GAGGGCTACA

GCTACCTGTA TATCAAGGGC AGCCAGCCCG AGGACAGCGC

CACCTACCTG TGCGCCCGGA ACACCGGCAA CCAGTTCTAC

TTTGGCACCG GCACCTCCCT GACCGTGATC CCCAACATCC

AGAACCCCGA CCCCGCGGTG TACCAGCTGA AGGACCCCAG

AAGCCAGGAC AGCACCCTGT GCCTGTTCAC CGACTTCGAC

AGCCAGATCA ACGTGCCCAA GACAATGGAA AGCGGCACCT

TCATCACCGA CAAGTGCGTG CTGGACATGA AGGCTATGGA

CAGCAAGAGC AACGGCGCCA TCGCCTGGTC CAACCAGACC

TCCTTCACAT GCCAAGACAT CTTCAAAGAG ACCAACGCCA

CCTACCCCAG CAGCGACGTG CCCTGCGATG CCACTCTCAC

CGAGAAGAGC TTCGAGACCC ACATGAACCT GAACTTCCAG

AACCTGAGCG TGATGGGCCT GAGAATCCTG CTCCTGAAAG

TGGCCGGCTT CAACCTGCTG ATGACCCTGC GGCTCTGGAG

TTCTGGCAGC GGCGCTACCA ACTTCAGCCT GCTGAAGCAG

GCCGGCGACG TGGAGGAAAA CCCTGGCCCC ATGGTGATCG

GCCTGCTGTG CTGTGCCGCC CTGAGCCTGC TGTGGGCCGG

ACCTGTGAAC GCCGGCGTGA CCCAGACCCC CAAGTTCCAG

GTGCTGAAAA CCGGCCAGAG CATGACCCTG CAGTGCGCCC

AGGACATGAA CCACGAGTAC ATGAGCTGGT ACAGGCAGGA

CCCCGGCATG GGCCTGCGGC TGATCCACTA CAGCGTGGGA

GCCGGCATCA CCGACCAGGG CGAGGTGCCC AACGGCTACA

ACGTGAGCAG AAGCACCACC GAGGACTTCC CCCTGCGGCT

GCTGTCTGCC GCCCCTAGCC AGACCAGCGT GTACTTCTGC

GCCAGCAGCT TCCAGACCGG CGCCAGCTAC GGCTACACCT

TCGGCAGCGG CACCCGGCTG ACCGTGCTCG AGGACCTGCG

GAACGTGACC CCCCCCAAGG TGTCCCTGTT CGAGCCCAGC

AAGGCCGAGA TCGCCAACAA GCAGAAAGCC ACACTGGTCT

GTCTGGCTAG GGGCTTCTTC CCCGACCACG TGGAGCTGTC

TTGGTGGGTC AACGGCAAAG AAGTCCATAG CGGCGTCTGC

ACCGACCCTC AGGCTTACAA AGAGAGCAAC TACTCCTACT

GCCTGAGCAG CCGGCTGAGA GTGAGCGCCA CCTTCTGGCA

CAACCCCCGG AACCACTTCC GGTGCCAGGT GCAGTTCCAC

GGCCTGAGCG AAGAGGACAA GTGGCCTGAG GGCTCCCCCA

AGCCCGTGAC CCAGAACATC AGCGCCGAGG CCTGGGGCAG

AGCCGACTGC GGCATCACCA GCGCCAGCTA CCACCAGGGC

GTGCTGTCCG CCACCATCCT GTACGAGATC CTGCTGGGCA

AGGCCACACT GTACGCCGTG CTGGTGTCCG GCCTGGTCCT

GATGGCTATG GTGAAGAAGA AGAACAGCTG A
```

The nucleotide sequence may comprise the part(s) of the above sequence which encode one or more CDRs or a variant thereof having at least 70%, 80%, 90%, or 95% amino acid sequence identity, these parts are the following sections of SEQ ID No. 9:

CDR1α: 17-159
CDR2α: 241-258
CDR3α: 364-426
CDR1β: 1006-1020
CDR2β: 1072-1089
CDR3β: 1201-1269

The nucleotide sequence may comprise the part(s) of the above sequence which encode one or more variable regions or a variant thereof having at least 70%, 80%, 90%, or 95% amino acid sequence identity, these parts are:

Vα: 1-396
V β: 870-1269

The nucleotide sequence may comprise the part(s) of the above sequence which encode the α chain and/or the β chain or a variant thereof having at least 70%, 80%, 90%, or 95% amino acid sequence identity, these parts are:

α—1-780
β—870-1791.

The variant sequences may have additions, deletions or substitutions or one or more bases. If the variation involves addition(s) or deletion(s) they may either occur in threes or be balanced (i.e. an addition for each deletion) so that the variation does not cause a frame-shift for translation of the remainder of the sequence.

Some or all of the variations may be "silent" in the send that they do not affect the sequence of the encoded protein due to the degeneracy of the protein code.

Some or all of the variations may produce conservative amino acid substitutions as explained above. The variation may be concentrated in one or more regions, such as the regions encoding the constant regions, the linker, or the framework regions of the α or β clains, or they may be spread throughout the molecule.

The variant sequence should retain the capacity to encode all or part of a sequence which binds an NLVPMVATV:MHC complex.

Vector

The present invention also provides a vector comprising a nucleotide sequence according to the second aspect of the invention.

The term "vector" includes an expression vector i.e. a construct capable of in vivo or in vitro/ex vivo expression.

Viral delivery systems include but are not limited to adenovirus vector, an adeno-associated viral (AAV) vector, a herpes viral vector, retroviral vector, lentiviral vector, baculoviral vector.

Retroviruses are RNA viruses with a life cycle different to that of lytic viruses. In this regard, a retrovirus is an infectious entity that replicates through a DNA intermediate. When a retrovirus infects a cell, its genome is converted to a DNA form by a reverse transcriptase enzyme. The DNA copy serves as a template for the production of new RNA genomes and virally encoded proteins necessary for the assembly of infectious viral particles.

There are many retroviruses, for example murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

Lentiviruses also belong to the retrovirus family, but they can infect both dividing and non-dividing cells (Lewis et al (1992) EMBO J. 3053-3058).

The vector may be capable of transferring a nucleotide according to the second aspect of the invention to a cell, such as a T-cell, such that the cell expresses a CMV-specific TCR. The vector should ideally be capable of sustained high-level expression in T cells, so that the introduced TCR may compete successfully with the endogenous TCR for a limited pool of CD3 molecules.

The vector may be a retroviral vector. The vector may be based on or derivable from the MP71 vector backbone. The vector may lack a full-length or truncated version of the Woodchuck Hepatitis Response Element (WPRE).

For efficient infection of human cells, viral particles may be packaged with amphotropic envelopes or gibbon ape leukemia virus envelopes.

Increasing the supply of CD3 molecules may increase TCR expression in gene modified cells. The vector may therefore also comprise the genes for CD3-gamma, CD3-delta, CD3-epsilon and/or CD3-zeta. The vector may just comprise the gene for CD3-zeta. The genes may be linked by self-cleaving sequences, such as the 2A self-cleaving sequence. Alternatively one or more separate vectors may be provided encoding CD3 gene for co-transfer with the TCR-encoding vector(s).

Cell

The fourth aspect of the present invention relates to a cell which comprises a nucleotide sequence according to the second aspect of the invention. The cell may express a T-cell receptor of the first aspect of the invention.

The cell may be a T-cell. The cell may be derived from a T-cell isolated from a subject. The T-cell may be part of a mixed cell population isolated from the subject, such as a population of peripheral blood lymphocytes (PBL). T cells within the PBL population may be activated by methods known in the art, such as using anti-CD3 and CD28 antibodies.

The T-cell may be a CD4+ helper T cell or a CD8+ cytotoxic T cell. The cell may be in a mixed population of CD4+ helper T cell/CD8+ cytotoxic T cells. Polyclonal activation, for example using anti-CD3 antibodies optionally in combination with anti-CD28 antibodies will trigger the proliferation of CD4+ and CD8+ T cells, but may also trigger the proliferation of CD4+25+ regulatory T-cells. TCR gene transfer into regulatory T cells is undesirable as they may suppress the anti-viral activity of the gene-modified cytotoxic and helper T cells. The CD4+CD25+ population may therefore be depleted before TCR gene transfer.

The present invention also provides a method of producing a cell according to the fourth aspect of invention which comprises the step of transfecting or transducing a cell in vitro or ex vivo with a vector according to the third aspect of the invention.

The cell may be isolated from the subject to which the genetically modified cell is to be adoptively transferred. In this respect, the cell may be made by isolating a T-cell from a subject, optionally activating the T-cell, TCR gene transfer ex vivo and subsequent immunotherapy of the subject by adoptive transfer of the TCR-transduced cells.

Alternatively the cell may be isolated from a different subject, such that it is allogeneic. The cell may be isolated from a donor subject. For example, if the subject is undergoing allogeneic haematopoietic stem cell transplantation (Allo-HSCT) or solid organ transplantation or cell transplantation or stem cell therapy, the cell may be derived from the donor, from which the organs, tissues or cells are derived. The donor may be a CMV seronegative donor. The donor and the subject undergoing treatment may be siblings. The donor may be CMV seronegative.

Alternatively the cell may be, or be derived from, a stem cell, such as a haemopoietic stem cell (HSC). Gene transfer into HSCs does not lead to TCR expression at the cell surface as stem cells do not express the CD3 molecules. However, when stem cells differentiate into lymphoid precursors that migrate to the thymus, the initiation of CD3 expression leads to the surface expression of the introduced TCR in thymocytes.

An advantage of this approach is that the mature T cells, once produced, express only the introduced TCR and little or no endogenous TCR chains, because the expression of the introduced TCR chains suppresses rearrangement of endogenous TCR gene segments to form functional TCR alpha and beta genes.

A further benefit is that the gene-modified stem cells are a continuous source of mature T-cells with the desired antigen specificity. The cell may therefore be a gene-modified stem cell, which, upon differentiation, produces a T-cell expressing a TCR of the first aspect of the invention. The present invention also provides a method of producing a T-cell expressing a TCR of the first aspect of the invention by inducing the differentiation of a stem cell which comprises a nucleotide sequence according to the second aspect of the invention.

A disadvantage of the stem cell approach is that TCRs with the desired specificity may get deleted during T-cell development in the thymus or may induce tolerance when expressed in peripheral T-cells. Another possible issue is the risk of insertional mutagenesis in stem cells.

CMV-Associated Diseases

The present invention also relates to a method for treating and/or preventing a disease associated with CMV in a subject which comprises the step of adoptive transfer of a CMV-specific T-cell to the subject.

The CMV-specific T-cell may recognise the major CMV matrix phosphoprotein pp65. The CMV-specific T cell may recognise the epitope NLVPMVATV.

The TCR may, for example be HLA-A*01, A*02, A*03, A*11 or A*24 restricted. The TCR may be HLA-A*0201 restricted.

The term 'preventing' is intended to refer to averting, delaying, impeding or hindering the contraction of the disease. The treatment may, for example, prevent or reduce the likelihood of CMV infection and/or reactivation.

'Treating' as used herein refers to caring for a diseased subject, in order to ameliorate, cure or reduce the symptoms of the disease, or reduce or halt the progression of the disease. It also refers to treatment which renders the virally-infected subject non-infectious to other subjects.

CMV is a ubiquitous human herpes virus that infects approximately 50% of normal individuals. In the majority of cases the immune response is able to control acute infection by recognising CMV derived antigens. The virus then persists for the life of the host in a latent state. Outgrowth is prevented by immune system effector mechanisms including neutralising antibodies to virus membrane proteins, HLA-restricted CMV-specific helper and cytotoxic T cells, and MHC-unrestricted effectors.

CMV infection is important to certain high-risk groups. Major areas of risk of infection include pre-natal or postnatal infants and immunocompromised individuals, such as organ transplant recipients, persons with leukemia, or those infected with human immunodeficiency virus (HIV). In HIV infected persons, CMV is considered an AIDS-defining infection, indicating that the T-cell count has dropped to low levels.

Physicians recognize three clinical forms of CMV. These include: (1) CMV inclusion disease of the newborn, which ranges in severity from being without symptoms to being a severe disease affecting the liver, spleen and central nervous system, with possible developmental disabilities; (2) Acute acquired CMV infection, which is similar to infectious mononucleosis and characterized by fever, malaise, skeletal-muscular pain and the absence of a sore throat; (3) CMV in immunocompromised persons (for instance, people who have had organ transplants or who have HIV) with increased risk for difficult eye infections (CMV retinitis), gastrointestinal CMV, and encephalitis.

The most common types of infections by CMV can be group as follows:
Fetus/Infant:
  Congenital CMV infection
  Perinatal CMV infection
Immunocompetent patient:
  CMV mononucleosis
  Post-transfusion CMV
Immunocompromised patient:
  CMV pneumonitis
  CMV GI disease
  CMV retinitis The subject may be a human subject. In particular the subejct may be a foetus or a newborn baby, or an immunocompromised individual. Immunocompromised individuals include subjects with leukemia or AIDS or an immunosuppressed individual such as a transplant recipient.

The subject may be HLA-A*0201 positive. The subject may be CMV seropositive.

The method may be used in combination with traditional antiviral therapies such as the use of anti-viral drugs (Ganciclovir™, Foscarnet™).

ALLO-HSCT

The method of the invention may be used to treat and/or prevent reactivation of latent CMV post allogeneic haematopoietic stem cell transplantation.

Hematopoietic stem cell transplantation (HSCT) is the transplantation of blood stem cells derived from the bone marrow or blood. Stem cell transplantation is most often performed for people with diseases of the blood, bone marrow, or certain types of cancer.

With the availability of the stem cell growth factors GM-CSF and G-CSF, most hematopoietic stem cell transplantation procedures are now performed using stem cells collected from the peripheral blood, rather than from the bone marrow. Collecting peripheral blood stem cells provides a bigger graft, does not require that the donor be subjected to general anesthesia to collect the graft, results in a shorter time to engraftment, and may provide for a lower long-term relapse rate.

Hematopoietic stem cell transplantation remains a risky procedure with many possible complications; it has traditionally been reserved for patients with life-threatening diseases. While occasionally used experimentally in nonmalignant and nonhematologic indications such as severe disabling autoimmune disease and cardiovascular disease, the risk of fatal complications appears too high to gain wider acceptance.

Many recipients of HSCTs are multiple myeloma or leukemia patients who would not benefit from prolonged treatment with, or are already resistant to, chemotherapy. Candidates for HSCTs include pediatric cases where the patient has an inborn defect such as severe combined immunodeficiency or congenital neutropenia with defective stem cells, and also children or adults with aplastic to anemia who have lost their stem cells after birth. Other conditions treated with stem cell transplants include sickle-cell disease, myelodysplastic syndrome, neuroblastoma, lymphoma, Ewing's Sarcoma, Desmoplastic small round cell tumor and Hodgkin's disease. More recently non-myeloablative, or so-called "mini transplant," procedures have been developed that require smaller doses of preparative chemo and radiation. This has allowed HSCT to be conducted in the elderly and other patients who would otherwise be considered too weak to withstand a conventional treatment regimen.

In addition highly immunosuppressive (or T cell depleted) reduced intensity conditioning Allo-HSCTs have been developed. These approaches reduce the toxicity of transplantation in older patients with more co-morbidities.

Allogeneic HSCT involves two people: the (healthy) donor and the (patient) recipient. Allogeneic HSC donors must have a tissue (HLA) type that matches the recipient. Matching is performed on the basis of variability at three or more loci of the (HLA) gene, and a perfect match at these loci is preferred. Even if there is a good match at these critical alleles, the recipient will require immunosuppressive medications to mitigate graft-versus-host disease. Allogeneic transplant donors may be related (usually a closely HLA matched sibling), syngeneic (a monozygotic or 'identical' twin of the patient—necessarily extremely rare since few patients have an identical twin, but offering a source of perfectly HLA matched stem cells) or unrelated (donor who is not related and found to have very close degree of HLA matching). About 25 to 30% of allogeneic HSCT recipients have an HLA-identical sibling. Allogeneic transplants are also performed using umbilical cord blood as the source of stem cells. In general, by transplanting healthy stem cells to the recipient's immune system, allogeneic HCSTs appear to improve chances for cure or long-term remission once the immediate transplant-related complications are resolved.

A compatible donor is found by doing additional HLA-testing from the blood of potential donors. The HLA genes fall in two categories (Type I and Type II). In general, mismatches of the Type-I genes (i.e. HLA-A, HLA-B, or HLA-C) increase the risk of graft rejection. A mismatch of an HLA Type II gene (i.e. HLA-DR, or HLA-DQB1) increases the risk of graft-versus-host disease. In addition a genetic mismatch as small as a single DNA base pair is significant so perfect matches require knowledge of the exact DNA sequence of these genes for both donor and recipient. Leading transplant centers currently perform testing for all five of these HLA genes before declaring that a donor and recipient are HLA-identical.

In the case of a bone marrow transplant, the HSC are removed from a large bone of the donor, typically the pelvis, through a large needle that reaches the center of the bone. The technique is referred to as a bone marrow harvest and is performed under general anesthesia.

Peripheral blood stem cells are now the most common source of stem cells for allogeneic HSCT. They are usually collected from the blood by apheresis. The donor's blood is withdrawn through a sterile needle in one arm and passed through a machine that removes white blood cells. The red blood cells are returned to the donor. The peripheral stem cell yield is boosted with daily subcutaneous injections of Granulocyte-colony stimulating factor, serving to mobilize stem cells from the donor's bone marrow into the peripheral circulation.

CMV disease in Allo-HSCT Recipients is thought to result primarily from reactivation of latent virus. Transmission of the virus can occur from donor marrow infusion or from allogeneic blood products. In immunocompromised bone marrow transplant recipients, virus reactivation frequently leads to progressive CMV infection, which is a major cause of infectious morbidity and mortality in this group of patients. Progressive CMV infection is a consequence both of the immunosuppression and the delayed immune reconstitution in these patients following transplant.

In the method of the present invention donor-derived T-cells are transduced ex vivo with gene(s) encoding a CMV-specific T-cell receptor using, for example, a retroviral vector. The donor-derived CMV-specific T cells are then used for adoptive immunotherapy for a recipient of Allo-HSCT.

The method may involve the adoptive transfer of both CD8+ and CD4+ CMV-specific T cells, for example as a mixed population. It is thought that the provision of help from CD4+ T cells improves the CTL response and makes it more efficient. It is possible to redirect the specificity of a CD4+ helper T cell using MHC class I-restricted CMV-specific TCR. It may also be necessary to transfer the CD8 gene into the helper T-cell if the TCR is CD8-dependent.

A quantitative PCR-based assay is used as part of routine clinical practice to determine CMV viral load following Allo-HSCT. Where either the patient or donor are CMV seropositive prior to transplant, it has been shown that in excess of 60% of patients became PCR positive at some point following the transplant with myeloablative conditioning and up to 85% with reduced intensity conditioning incorporating T cell depletion. This assay is used as an indicator for initiation of antiviral drug therapy.

The same, or an equivalent assay for monitoring viral load may be used in connection with the method of the present invention
(i) before treatment, to determine the appropriate time for treatment; and/or
(ii) after treatment, to analyse the effect effect of the adoptively transferred CMV specific T cells to be monitored.

The invention will now be further described by way of Examples, which are meant to serve to assist one of ordinary skill in the art in carrying out the invention and are not intended in any way to limit the scope of the invention.

EXAMPLES

Example 1

Construction of a Retroviral Vector to Deliver CMV-Specific TCR Genes

An important issue for TCR gene therapy is the selection of vectors capable of sustained high-level expression in T lymphocytes. High expression levels are required to allow the introduced TCR to compete with the endogenous TCR for a limited pool of CD3 molecules. Further requirements for TCR gene therapy are (i) a transduction efficiency of up to 30% with minimal ex vivo manipulation, (ii) the absence of replication competent vectors, and (iii) stable TCR expression over time to allow for memory development.

In this study the MP71 vector backbone was used with a codon-optimised TCR sequence and an additional cysteine in each alpha and beta chain constant region to enhance gene expression and minimize mis-pairing with endogenous TCR chains. The MP71 vector backbone has been described previously (Hildigner et al (1999) J. Virol. 73:4083-4089). The LTR of the MP71 vector is derived from the Myeloproliferative Sarcroma Virus (MPSV) and the leader sequence (LS) is derived from the Mouse Embryonic Stem Cell Virus (MESV). The leader sequence was designed to increase vector safety in clinical applications. All ATG codons have been removed to decrease the risk of possible protein/peptide production and reduce the likelihood of homologous recombination with endogenous retroviral sequences. The expression of genes inserted into MP71 is enhanced by a minimal splice acceptor site at the 3' end of the leader sequence. The original MP71 vector contained a full length Woodchuck Hepatitis Response Element (WPRE) to enhance gene expression at the post-transcriptional level. The MP71 vector containing a truncated WPRE with mutated ATG codons is currently used in Germany in a clinical trial using gene-modified T cells in HIV patients.

The present inventors have further modified the MP71 vector and tested variants without any WPRE sequences. The vector comprises the CMV TCR alpha and beta genes, linked via an internal self-cleaving porcine teschovirus 2A sequence, as shown in FIG. 1. The alpha and beta TCR genes were synthesised based on dominant TCR usage by HLA-A*0201 restricted CMV pp65-specific CTL clones. The amino acid sequence for the TCR alpha-2A-TCR beta product is given as SEQ ID No. 8 and its coding sequence given as SEQ ID No. 9.

Example 2

Production of CMV pp65-Specific TCR-Transduced Human T Cells

Human T cell receptor (TCR) genes specific for CMV were transduced into human T cells by using retroviral vectors carrying the desired TCR genes. Briefly, amphotropic packaging cells expressing the retroviral gag-pol genes were transfected with the specified TCR-retroviral vectors by using calcium phosphate precipitation method. After the retroviral transfection, the transfection medium was changed into human T cell medium for the harvesting of retroviral supernatant. The collected retroviral supernatant containing the viral particles expressing the desired TCR genes were then used to infect/transduce activated human T cells. 24 hours later, the introduced TCR genes are expressed on the surface of transduced T cells, and can be detected by FACS staining.

Figure 2:
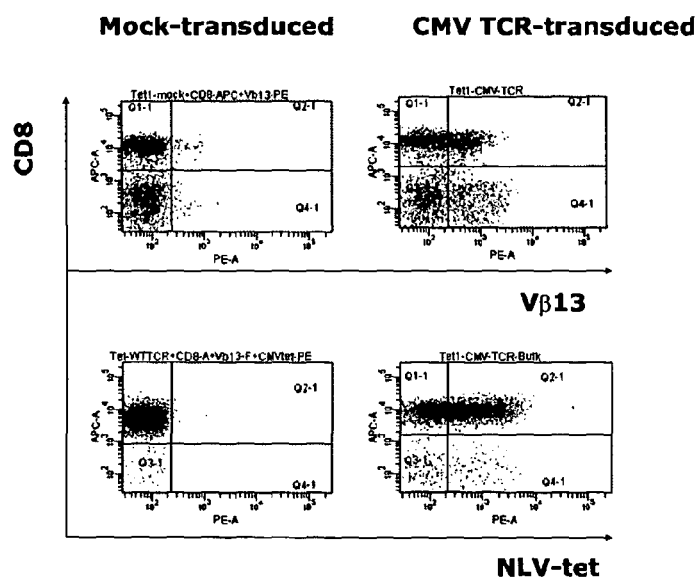
FIG. 2—CMV TCR-transduced human T cells can be identified by anti-Vβ13 antibodies (upper panel). CMV TCR-transduced T cells bind specific tetramer and can be expanded in vitro (lower panel).

As shown in FIG. 2, retroviral transfer of the CMV pp65-specific TCR results in TCR expression on the surface of recipient T cells as determined by peptide/MHC tetramer staining and anti-Vβ13 antibody staining.

Figure 4:
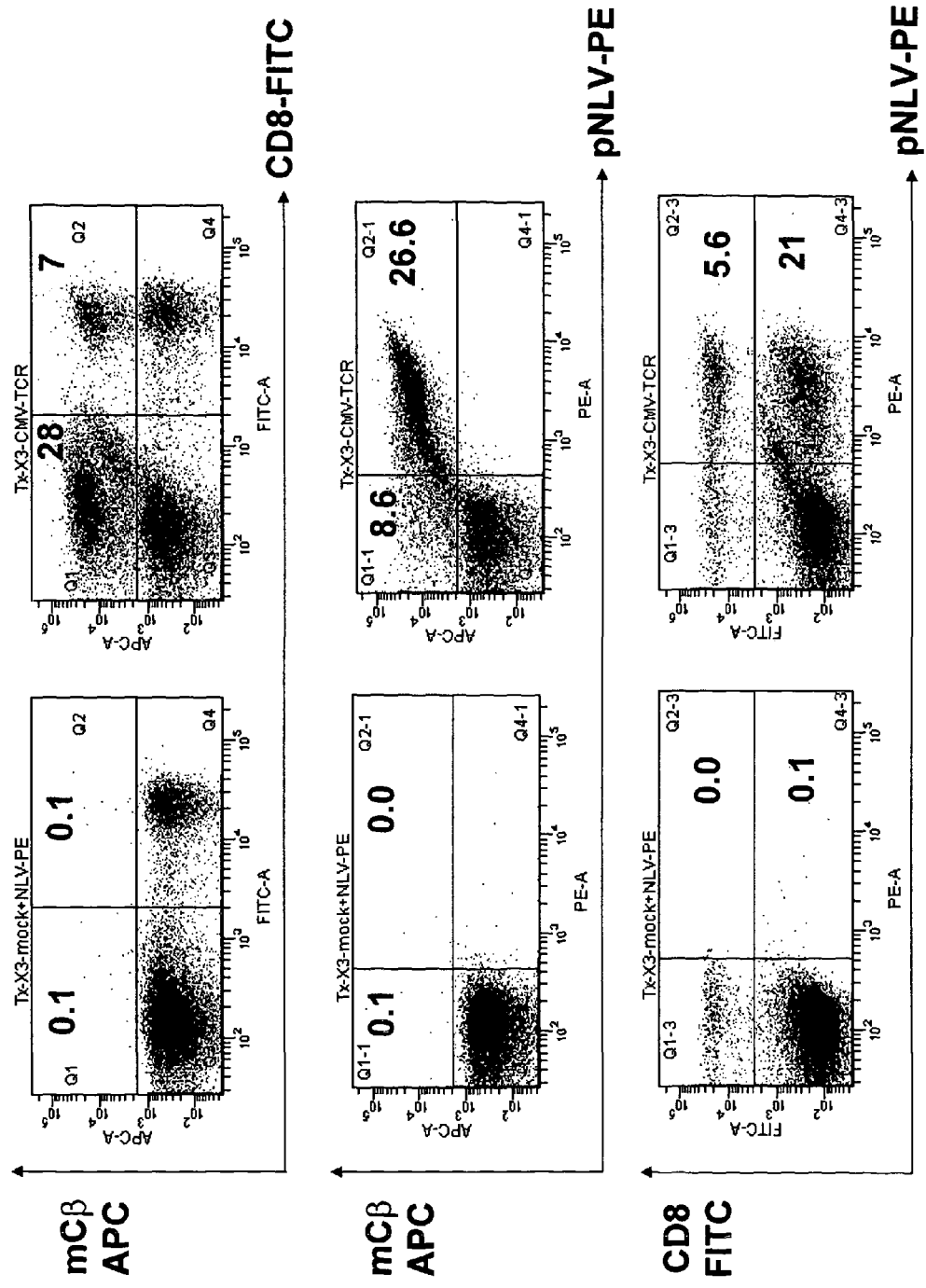
FIG. 4—CMV-TCR transduction of X3-PBMC

FIGS. 2 and 4 also shows that CMV TCR-transduced T cells can be expanded in vitro.

Example 3

Intracellular Cytokine Staining of TCR Transduced T Cells

To demonstrate the functional antigen specific activity, the present inventors performed antigen specific stimulation and intracellular cytokine staining assays.

TCR-transduced T cells ($2 \times 10^5$) were incubated with $2 \times 10^5$ T2 stimulator cells coated with 100 mM relevant (pNLV: NLVPMVATV) or irrelevant (pCLG: CLG-GLLTMV) peptide in 200 ml of culture medium containing brefeldin A (Sigma-Aldrich) at 1 mg/ml. After an incubation period of 18 h at 37° C. with 5% $CO_2$, the cells were first stained for surface CD8 or CD4 and then fixed, permeabilized, and stained for intracellular IFNg, IL2 and TNFa using the Fix & Perm kit (Caltag) according to the manufacturer's instructions. Samples were acquired on a LSR II flow cytometer and the data was analyzed using FACSDiva software (BD Biosciences).

Figure 3:
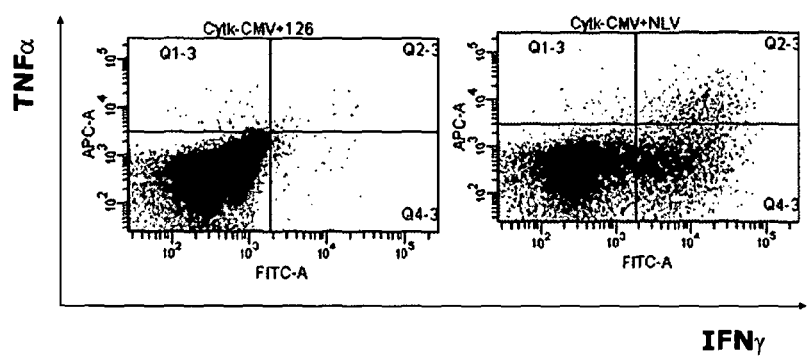
FIG. 3—HLA-A*0201-restricted CMV pp65-specific cytokine secretion by CMV TCR-transduced human T cells.
Figure 5:
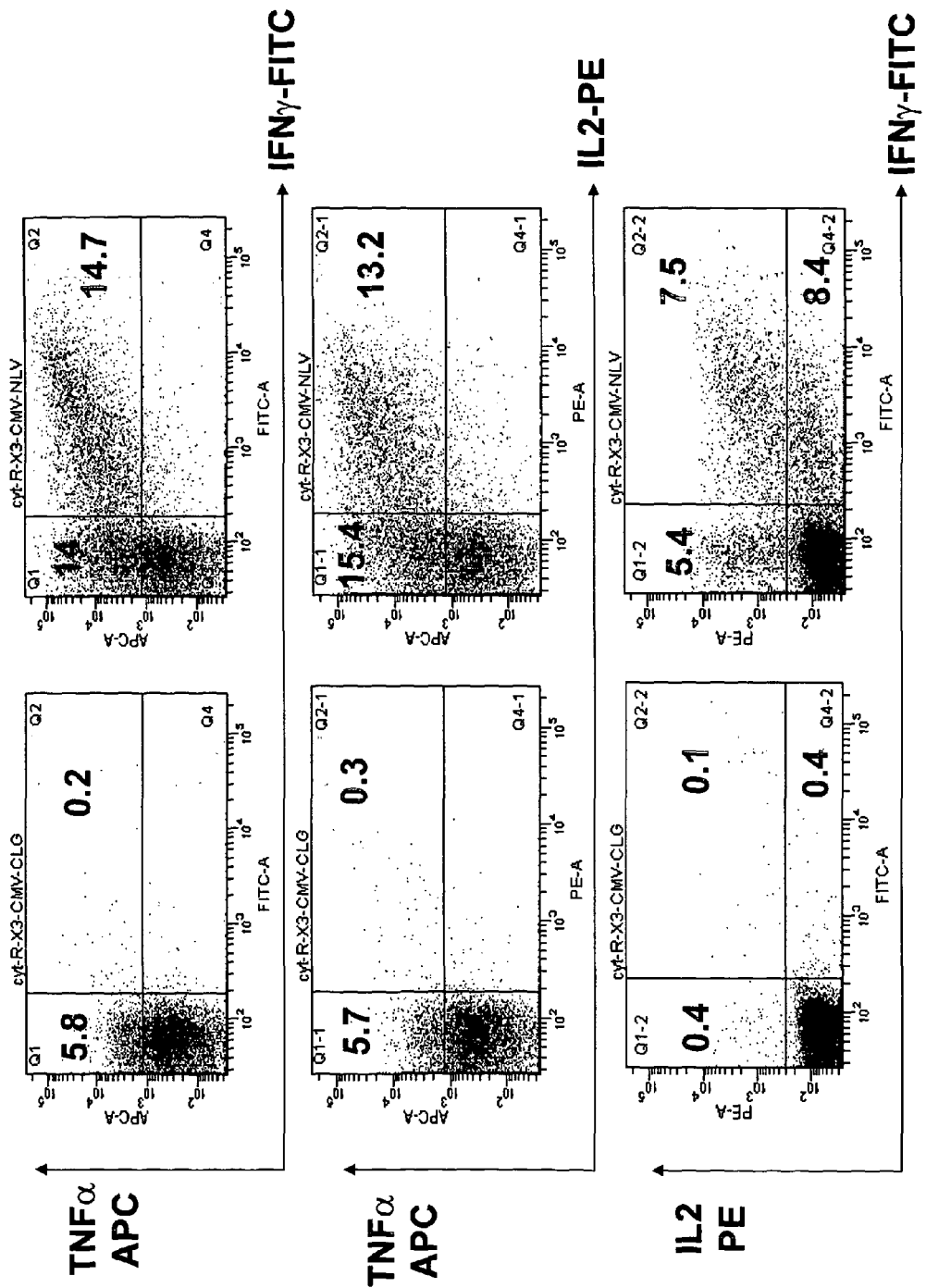
FIG. 5—CMV-TCR-X3-CD4-cytk
Figure 6:
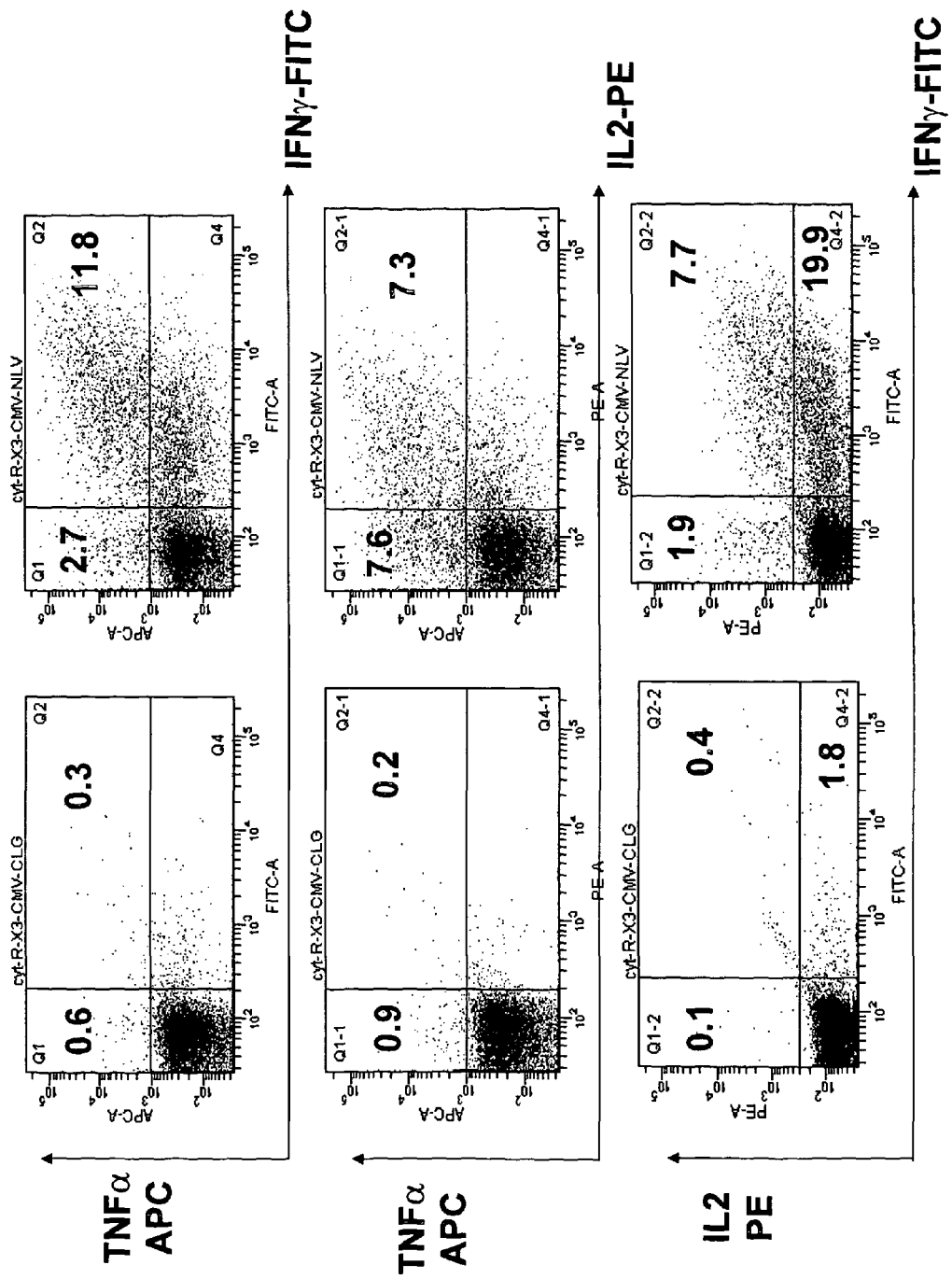
FIG. 6—CMV-TCR-X3-CD8-cytk

The results are shown in FIGS. 3, 5 and 6.

Example 4

The Use of CMV TCR-Transduced T Cells to Generate a CMV Immune Response after Allogeneic HSCT An HLA-A*0201-restricted CMV pp65-specific T cell receptor (TCR) is introduced into donor T cells via ex vivo GMP retroviral transduction. Donor T cells are isolated from peripheral blood following a simple venesection procedure. The collected T cells are cultured for 7 days in vitro for transduction with replication defective retroviral vectors containing the CMV-specific TCR. The CMV TCR-transduced T cells will be resuspended in a volume of 5-20 ml.

The CMV TCR-transduced T cells are tested for TCR expression, CMV-specific cytokine secretion and microbiological contamination before being frozen and stored at −80° C. CMV seropositive transplant recipients are tested weekly for CMV reactivation by quantitative PCR on peripheral blood. On first detection of CMV DNA≥200 copies/ml, $10^5$ bulk CMV TCR-transduced T cells/kg recipient weight is infused into the patient.

Blood is taken regularly to determine persistence and expansion of the CMV TCR-transduced T cells.

T cells are collected, washed, counted and analysed by flow cytometry for expression of CMV TCR on cell surface using antibodies against CD3, CD8 and Vβ13.1 (and tetramer staining). To determine the percentage of T cells expressing endogenous Vβ13.1 untransduced T cells are stained with antibodies against CD3, CD8 and Vβ13.1. The staining results allow the percentage and number of TCR transduced T cells to be determined. T cells are stimulated with CMV pp65 peptide and control peptides to monitor antigen-specific immune responses.

CMV-specific immune responses of TCR-transduced T cells pre- and post-infusion are analysed using in vitro functional assays such as intracellular cytokine secretion, elispot, proliferation and cytotoxicity assays. Anti-CMV responses are analysed post infusion of CMV TCR-transduced T cells using serial quantitative PCR for viral copy numbers in peripheral blood.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. An isolated T-cell receptor (TCR) which binds to a peptide from the cytomegalovirus (CMV) phosphoprotein pp65 having the amino acid sequence NLVPMVATV (SEQ ID NO: 1) when presented by a major histocompatibility complex (MHC) molecule, the TCR comprising an α chain and a β chain, wherein the α chain comprises three complementarity determining regions (CDRs) having the following amino acid sequences:

CDR1α - SSNFYA,  (SEQ ID NO: 4)

CDR2α - MTLNGD,  (SEQ ID NO: 5)
and

CDR3α - ARNTGNQFYFGTGTSLTVIPN,  (SEQ ID NO: 2)
and wherein the β chain comprises three complementarity determining regions (CDRs) having the following amino acid sequences:

CDR1β - MNHEY,  (SEQ ID NO: 6)

CDR2β - SVGAGI,  (SEQ ID NO: 7)
and

CDR3β - ASSFQTGASYGYTFGSGTRLTVL.  (SEQ ID NO: 3)

2. The TCR according to claim 1 which comprises the amino acid sequence shown as SEQ ID NO: 8 or a variant thereof having at least 80% amino acid sequence identity.

3. The TCR according to claim 1 which comprises one or more mutations at the TCR α chain/β chain interface, such that when the TCR α chain and β chain are expressed in a T-cell, the frequency of mis-pairing between these chains and the endogenous TCR α chain and β chain is reduced.

4. The TCR according to claim 3, wherein the constant region domains of the α chain and β chain each comprise an additional cysteine residue, enabling the formation of an extra disulphide bond between the α chain and the β chain.

\* \* \* \* \*

```
SEQUENCE LISTING

<160> NUMBER OF SEQ ID NOS: 12

<210> SEQ ID NO 1
<211> LENGTH: 9
<212> TYPE: PRT
<213> ORGANISM: Cytomegalovirus (CMV)

<400> SEQUENCE: 1

Asn Leu Val Pro Met Val Ala Thr Val
1               5

<210> SEQ ID NO 2
<211> LENGTH: 21
<212> TYPE: PRT
<213> ORGANISM: Homo sapiens

<400> SEQUENCE: 2

Ala Arg Asn Thr Gly Asn Gln Phe Tyr Phe Gly Thr Gly Thr Ser Leu
1               5                   10                  15

Thr Val Ile Pro Asn
            20

<210> SEQ ID NO 3
<211> LENGTH: 23
<212> TYPE: PRT
<213> ORGANISM: Homo sapiens

<400> SEQUENCE: 3

Ala Ser Ser Phe Gln Thr Gly Ala Ser Tyr Gly Tyr Thr Phe Gly Ser
1               5                   10                  15

Gly Thr Arg Leu Thr Val Leu
            20
```

```
<210> SEQ ID NO 4
<211> LENGTH: 6
<212> TYPE: PRT
<213> ORGANISM: Homo sapiens

<400> SEQUENCE: 4

Ser Ser Asn Phe Tyr Ala
1               5

<210> SEQ ID NO 5
<211> LENGTH: 6
<212> TYPE: PRT
<213> ORGANISM: Homo sapiens

<400> SEQUENCE: 5

Met Thr Leu Asn Gly Asp
1               5

<210> SEQ ID NO 6
<211> LENGTH: 5
<212> TYPE: PRT
<213> ORGANISM: Homo sapiens

<400> SEQUENCE: 6

Met Asn His Glu Tyr
1               5

<210> SEQ ID NO 7
<211> LENGTH: 6
<212> TYPE: PRT
<213> ORGANISM: Homo sapiens

<400> SEQUENCE: 7

Ser Val Gly Ala Gly Ile
1               5

<210> SEQ ID NO 8
<211> LENGTH: 596
<212> TYPE: PRT
<213> ORGANISM: Homo sapiens

<400> SEQUENCE: 8

Met Glu Lys Asn Pro Leu Ala Ala Pro Leu Leu Ile Leu Trp Phe His
1               5                   10                  15

Leu Asp Cys Val Ser Ile Leu Asn Val Glu Gln Ser Pro Gln Ser Leu
                20                  25                  30

His Val Gln Glu Gly Asp Ser Thr Asn Phe Thr Cys Ser Phe Pro Ser
            35                  40                  45

Ser Asn Phe Tyr Ala Leu His Trp Tyr Arg Trp Glu Thr Ala Lys Ser
        50                  55                  60

Pro Glu Ala Leu Phe Val Met Thr Leu Asn Gly Asp Glu Lys Lys Lys
65                  70                  75                  80

Gly Arg Ile Ser Ala Thr Leu Asn Thr Lys Glu Gly Tyr Ser Tyr Leu
                85                  90                  95

Tyr Ile Lys Gly Ser Gln Pro Glu Asp Ser Ala Thr Tyr Leu Cys Ala
            100                 105                 110

Arg Asn Thr Gly Asn Gln Phe Tyr Phe Gly Thr Gly Thr Ser Leu Thr
        115                 120                 125

Val Ile Pro Asn Ile Gln Asn Pro Asp Pro Ala Val Tyr Gln Leu Lys
    130                 135                 140

Asp Pro Arg Ser Gln Asp Ser Thr Leu Cys Leu Phe Thr Asp Phe Asp
```

```
            145                 150                 155                 160
Ser Gln Ile Asn Val Pro Lys Thr Met Glu Ser Gly Thr Phe Ile Thr
            165                 170                 175

Asp Lys Cys Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
            210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Lys Val Ala Gly
            245                 250                 255

Phe Asn Leu Leu Met Thr Leu Arg Leu Trp Ser Ser Gly Ser Gly Ala
            260                 265                 270

Thr Asn Phe Ser Leu Leu Lys Gln Ala Gly Asp Val Glu Glu Asn Pro
            275                 280                 285

Gly Pro Met Val Ile Gly Leu Leu Cys Cys Ala Ala Leu Ser Leu Leu
            290                 295                 300

Trp Ala Gly Pro Val Asn Ala Gly Val Thr Gln Thr Pro Lys Phe Gln
305                 310                 315                 320

Val Leu Lys Thr Gly Gln Ser Met Thr Leu Gln Cys Ala Gln Asp Met
            325                 330                 335

Asn His Glu Tyr Met Ser Trp Tyr Arg Gln Asp Pro Gly Met Gly Leu
            340                 345                 350

Arg Leu Ile His Tyr Ser Val Gly Ala Gly Ile Thr Asp Gln Gly Glu
            355                 360                 365

Val Pro Asn Gly Tyr Asn Val Ser Arg Ser Thr Thr Glu Asp Phe Pro
            370                 375                 380

Leu Arg Leu Leu Ser Ala Ala Pro Ser Gln Thr Ser Val Tyr Phe Cys
385                 390                 395                 400

Ala Ser Ser Phe Gln Thr Gly Ala Ser Tyr Gly Tyr Thr Phe Gly Ser
            405                 410                 415

Gly Thr Arg Leu Thr Val Leu Glu Asp Leu Arg Asn Val Thr Pro Pro
            420                 425                 430

Lys Val Ser Leu Phe Glu Pro Ser Lys Ala Glu Ile Ala Asn Lys Gln
            435                 440                 445

Lys Ala Thr Leu Val Cys Leu Ala Arg Gly Phe Phe Pro Asp His Val
            450                 455                 460

Glu Leu Ser Trp Trp Val Asn Gly Lys Glu Val His Ser Gly Val Cys
465                 470                 475                 480

Thr Asp Pro Gln Ala Tyr Lys Glu Ser Asn Tyr Ser Tyr Cys Leu Ser
            485                 490                 495

Ser Arg Leu Arg Val Ser Ala Thr Phe Trp His Asn Pro Arg Asn His
            500                 505                 510

Phe Arg Cys Gln Val Gln Phe His Gly Leu Ser Glu Glu Asp Lys Trp
            515                 520                 525

Pro Glu Gly Ser Pro Lys Pro Val Thr Gln Asn Ile Ser Ala Glu Ala
            530                 535                 540

Trp Gly Arg Ala Asp Cys Gly Ile Thr Ser Ala Ser Tyr His Gln Gly
545                 550                 555                 560

Val Leu Ser Ala Thr Ile Leu Tyr Glu Ile Leu Leu Gly Lys Ala Thr
            565                 570                 575
```

```
Leu Tyr Ala Val Leu Val Ser Gly Leu Val Leu Met Ala Met Val Lys
            580                 585                 590
Lys Lys Asn Ser
        595

<210> SEQ ID NO 9
<211> LENGTH: 1791
<212> TYPE: DNA
<213> ORGANISM: Homo sapiens

<400> SEQUENCE: 9
atggaaaaga acccccctggc tgcacccctg ctgatcctgt ggttccacct ggactgcgtg      60
agcatcctga acgtggagca gagcccccag tctctgcatg tgcaggaagg cgacagcacc     120
aacttcacct gcagcttccc cagcagcaac ttctacgccc tgcactggta cagatgggag     180
accgccaaga gccccgaggc cctgttcgtg atgaccctga acggcgacga agaagaagaag    240 ggccggatca cgccacccct gaacaccaaa gagggctaca gctacctgta tatcaagggc     300
agccagcccg aggacagcgc cacctacctg tgcgcccgga caccggcaa ccagttctac      360 tttggcaccg gcacctccct gaccgtgatc cccaacatcc agaaccccga ccccgcggtg     420
taccagctga aggaccccag aagccaggac agcaccctgt gcctgttcac cgacttcgac     480
agccagatca cgtgcccaa gacaatggaa agcggcaccct tcatcaccga caagtgcgtg     540
ctggacatga aggctatgga cagcaagagc aacggcgcca tcgcctggtc caaccagacc     600
tccttcacat gccaagacat cttcaaagag accaacgcca cctacccag cagcgacgtg      660 ccctgcgatg ccactctcac cgagaagagc ttcgagaccg acatgaacct gaacttccag    720
aacctgagcg tgatgggcct gagaatcctg ctcctgaaag tggccggctt caacctgctg    780
atgaccctgc ggctctggag ttctggcagc ggcgctacca acttcagcct gctgaagcag    840
gccggcgacg tggaggaaaa ccctggcccc atggtgatcg gcctgctgtg ctgtgccgcc    900
ctgagcctgc tgtgggccgg acctgtgaac gccggcgtga cccagacccc caagttccag    960
gtgctgaaaa ccggccagag catgaccctg cagtgcgccc aggacatgaa ccacgagtac    1020
atgagctggt acaggcagga ccccggcatg ggcctgcggc tgatccacta cagcgtggga   1080
gccggcatca ccgaccaggg cgaggtgccc aacggctaca acgtgagcag aagcaccacc   1140
gaggacttcc ccctgcggct gctgtctgcc gcccctagcc agaccagcgt gtacttctgc   1200
gccagcagct tccagaccgg cgccagctac ggctacacct tcggcagcgg cacccggctg   1260
accgtgctcg aggacctgcg gaacgtgacc ccccccaagg tgtccctgtt cgagcccagc   1320
aaggccgaga tcgccaacaa gcagaaagcc acactggtct gtctggctag ggcttcttc    1380 cccgaccacg tggagctgtc ttggtgggtc aacggcaaag aagtccatag cggcgtctgc   1440
accgaccctc aggcttacaa agagagcaac tactcctact gcctgagcag ccggctgaga   1500
gtgagcgcca ccttctggca caaccccgg aaccacttcc ggtgccaggt gcagttccac    1560
ggcctgagcg aagaggacaa gtggcctgag gctcccccca gcccgtgac ccagaacatc     1620 agcgccgagg cctggggcag agccgactgc ggcatcacca cgccagcta ccaccagggc    1680 gtgctgtccg ccaccatcct gtacgagatc ctgctgggca aggccacact gtacgccgtg   1740
ctggtgtccg gcctggtcct gatggctatg gtgaagaaga agaacagctg a            1791

<210> SEQ ID NO 10
<211> LENGTH: 551
<212> TYPE: PRT
<213> ORGANISM: Cytomegalovirus (CMV)
```

<400> SEQUENCE: 10

```
Met Ala Ser Val Leu Gly Pro Ile Ser Gly His Val Leu Lys Ala Val
 1               5                  10                  15

Phe Ser Arg Gly Asp Thr Pro Val Leu Pro His Glu Thr Arg Leu Leu
            20                  25                  30

Gln Thr Gly Ile His Val Arg Val Ser Gln Pro Ser Leu Ile Leu Val
        35                  40                  45

Ser Gln Tyr Thr Pro Asp Ser Thr Pro Cys His Arg Gly Asp Asn Gln
50                  55                  60

Leu Gln Val Gln His Thr Tyr Phe Thr Gly Ser Glu Val Glu Asn Val
65                  70                  75                  80

Ser Val Asn Val His Asn Pro Thr Gly Arg Ser Ile Cys Pro Ser Gln
                85                  90                  95

Glu Pro Met Ser Ile Tyr Val Tyr Ala Leu Pro Leu Lys Met Leu Asn
            100                 105                 110

Ile Pro Ser Ile Asn Val His His Tyr Pro Ser Ala Ala Glu Arg Lys
        115                 120                 125

His Arg His Leu Pro Val Ala Asp Ala Val Ile His Ala Ser Gly Lys
130                 135                 140

Gln Met Trp Gln Ala Arg Leu Thr Val Ser Gly Leu Ala Trp Thr Arg
145                 150                 155                 160

Gln Gln Asn Gln Trp Lys Glu Pro Asp Val Tyr Tyr Thr Ser Ala Phe
                165                 170                 175

Val Phe Pro Thr Lys Asp Val Ala Leu Arg His Val Val Cys Ala His
            180                 185                 190

Glu Leu Val Cys Ser Met Glu Asn Thr Arg Ala Thr Lys Met Gln Val
        195                 200                 205

Ile Gly Asp Gln Tyr Val Lys Val Tyr Leu Glu Ser Phe Cys Glu Asp
210                 215                 220

Val Pro Ser Gly Lys Leu Phe Met His Val Thr Leu Gly Ser Asp Val
225                 230                 235                 240

Glu Glu Asp Leu Thr Met Thr Arg Asn Pro Gln Pro Phe Met Arg Pro
                245                 250                 255

His Glu Arg Asn Gly Phe Thr Val Leu Cys Pro Lys Asn Met Ile Ile
            260                 265                 270

Lys Pro Gly Lys Ile Ser His Ile Met Leu Asp Val Ala Phe Thr Ser
        275                 280                 285

His Glu His Phe Gly Leu Leu Cys Pro Lys Ser Ile Pro Gly Leu Ser
290                 295                 300

Ile Ser Gly Asn Leu Leu Met Asn Gly Gln Gln Ile Phe Leu Glu Val
305                 310                 315                 320

Gln Ala Ile Arg Glu Thr Val Glu Leu Arg Gln Tyr Asp Pro Val Ala
                325                 330                 335

Ala Leu Phe Phe Phe Asp Ile Asp Leu Leu Gln Arg Gly Pro Gln
            340                 345                 350

Tyr Ser Glu His Pro Thr Phe Thr Ser Gln Tyr Arg Ile Gln Gly Lys
        355                 360                 365

Leu Glu Tyr Arg His Thr Trp Asp Arg His Asp Glu Gly Ala Ala Gln
370                 375                 380

Gly Asp Asp Asp Val Trp Thr Ser Gly Ser Asp Ser Glu Glu Leu
385                 390                 395                 400

Val Thr Thr Glu Arg Lys Thr Pro Arg Val Thr Gly Gly Gly Ala Met
                405                 410                 415
```

```
Ala Gly Ala Ser Thr Ser Ala Gly Arg Lys Arg Lys Ser Ala Ser Ser
            420                 425                 430

Ala Thr Ala Cys Thr Ala Gly Val Met Thr Arg Gly Arg Leu Lys Ala
            435                 440                 445

Glu Ser Thr Val Ala Pro Glu Glu Asp Thr Asp Glu Asp Ser Asp Asn
            450                 455                 460

Glu Ile His Asn Pro Ala Val Phe Thr Trp Pro Pro Trp Gln Ala Gly
465                 470                 475                 480

Ile Leu Ala Arg Asn Leu Val Pro Met Val Ala Thr Val Gln Gly Gln
            485                 490                 495

Asn Leu Lys Tyr Gln Glu Phe Phe Trp Asp Ala Asn Asp Ile Tyr Arg
            500                 505                 510

Ile Phe Ala Glu Leu Glu Gly Val Trp Gln Pro Ala Ala Gln Pro Lys
            515                 520                 525

Arg Arg Arg His Arg Gln Asp Ala Leu Pro Gly Pro Cys Ile Ala Ser
            530                 535                 540

Thr Pro Lys Lys His Arg Gly
545                 550

<210> SEQ ID NO 11
<211> LENGTH: 16
<212> TYPE: PRT
<213> ORGANISM: Cytomegalovirus (CMV)

<400> SEQUENCE: 11

Gly Ile Leu Ala Arg Asn Leu Val Ala Thr Val Gln Gly Gln Asn Leu
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: Synthetic peptide

<400> SEQUENCE: 12

Cys Leu Gly Gly Leu Leu Thr Met Val
1               5
```